United States Patent [19]
Kobylinski et al.

[11] 3,947,483
[45] Mar. 30, 1976

[54] METAL CHRYSOTILE METHANE SYNTHESIS CATALYST

[75] Inventors: Thaddeus P. Kobylinski; Harold E. Swift, both of Gibsonia, Pa.

[73] Assignee: Gulf Research & Development Company, Pittsburgh, Pa.

[22] Filed: Dec. 16, 1974

[21] Appl. No.: 532,848

[52] U.S. Cl. .......................... 260/449 M; 260/449.6
[51] Int. Cl.² .......................................... C07C 1/04
[58] Field of Search ..................... 260/449 M, 449.6

[56] References Cited
UNITED STATES PATENTS

| | | | |
|---|---|---|---|
| 2,231,990 | 2/1941 | Dreyfus | 260/449 |
| 2,640,844 | 6/1953 | McGrath et al. | 260/449.6 |
| 3,600,145 | 8/1971 | Johnson et al. | 260/449.6 M |
| 3,729,429 | 4/1973 | Robson | 423/328 |

Primary Examiner—Howard T. Mars

[57] ABSTRACT

The conversion of carbon monoxide and hydrogen to produce methane is catalyzed by a layered complex metal silicate composition characterized as having repeating units of the structural formula $$[(1-x)Ni^a + xRu^b]_n (OH)_4Si_2O_5 \cdot wH_2O$$

where $x$ is a number from 0 to 1, this number expressing the atomic fraction of the metals nickel and ruthenium, $a$ is the valence of nickel, $b$ is the valence of ruthenium, $n$ is a number equal in value to that defined by the ratio $$6/[a(1-x) + bx]$$

and $w$ is a number ranging from 0 to 4. Nickel chrysotile is the preferred catalyst.

9 Claims, No Drawings

METAL CHRYSOTILE METHANE SYNTHESIS CATALYST

This invention relates to the conversion of carbon oxides such as carbon monoxide and carbon dioxide and hydrogen to methane using an improved metal chrysotile catalyst. In particular this invention relates to the use of nickel chrysotile or ruthenium chrysotile for the conversion of carbon monoxide and hydrogen to methane.

BACKGROUND OF THE INVENTION

The limited supplies of natural gas (methane) in the United States, together with its great usefulness, have provided the necessary incentive for the discovery and development of techniques to produce synthetic natural gas (SNG) by a reaction known as methanation. The methanation reaction generally involves the conversion of synthesis gas to methane and water in the presence of a suitable catalyst. Synthesis gas is a mixture of CO and hydrogen and can be produced by the gasification of coal with steam and oxygen. Suitable catalysts for methanation are described in the prior art and include iron, nickel and ruthenium, among others. The Bureau of Mines Report of Investigation 5137 entitled "Synthesis of Methane" by Murrat Greyson et al. (July 1955) reports that nickel is superior to iron and that the techniques of catalyst preparation determine to a large extent the process life of the nickel catalyst.

The nickel catalysts investigated by the Bureau and others are typically prepared by precipitating nickel salts such as nickel nitrate onto various supports such as alumina or kieselguhr. In addition to poor aging characteristics, prior art nickel catalysts suffer from their tendency to promote undesired side reactions such as the disproportionation of the CO to $CO_2$ and the formation of carbon either by the decomposition of CO or the formation of higher molecular weight hydrocarbons which eventually deposit and form coke.

A superior methanation catalyst has now been discovered which tends to avoid coke and the disproportionation of CO to $CO_2$ at high temperatures and in addition tends to maintain substantially complete conversion of CO in synthesis gas over longer periods of time at any given nickel level and temperature.

An improved methanation reaction is accomplished in accordance with the invention by contacting CO, $CO_2$, or mixtures of these carbon oxides and hydrogen wherein the molar ratio of hydrogen to the carbon oxides is at least 2:1 under methanation conditions in the presence of a catalyst comprising a crystalline layered complex metal silicate characterized as having repeating units having the structural formula:

$$8 [(1-x) Ni^a + xRu_b]_n (OH)_4Si_2O_5 \cdot wH_2O$$

where $x$ is a number from 0 to 1, this number expressing the atomic fraction of the metals nickel and ruthenium, $a$ is the valence of nickel, $b$ is the valence of ruthenium, $n$ is a number equal in value to that defined by the ratio

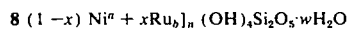

$$6/[a(1-x) + bx]$$

and $w$ is a number ranging from 0 to 4.

The improved methanation catalyst for use in the process of this invention is a known layered complex metal silicate wherein the metal is selected from nickel, ruthenium, or mixtures of these metals. These layered complex metal silicates and their methods of preparation are described, for example, in U.S. Pat. No. 3,729,429 to Robson issued Apr. 24, 1973. The specification of the Robson patent is incorporated herein by reference for the purpose of providing a fuller description of the catalyst and a method of preparing the catalyst. It is realized that the materials described by Robson encompass many complex metal silicates while only the nickel and ruthenium or mixed nickel-ruthenium complex metal silicates are claimed in this specification as useful materials to promote the methanation reaction. Robson in his specification describes his metal silicates as useful catalytic agents in hydrocarbon conversion reactions. Illustrative of such reactions are aromatization, isomerization, hydroisomerization, cracking, hydrocracking, polymerization, alkylation, dealkylation, hydrogenation and dehydrogenation, desulfurization, denitrogenation and reforming (see Col. 3, lines 14–18 of the '429 Robson patent). Nowhere does Robson teach or indicate that his materials, especially the nickel or ruthenium forms, are useful for the synthesis as contrasted with the conversion of hydrocarbons and in particular the synthesis of methane.

More specifically, the catalyst used to promote the desired methanation reaction in accordance with this invention is a crystalline layered complex metal silicate composition characterized as having repeating units having the structural formula $$[(1-x)Ni^a - xRu^b]_n (OH)_4Si_2O_5 \cdot wH_2O$$

where $x$ is a number from 0 to 1, this number expressing the atomic fraction of the metals nickel and ruthenium, $a$ is the valence of nickel, $b$ is the valence of ruthenium, $n$ is a number equal in value to that defined by the ratio

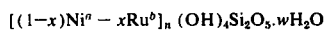

$$6/[a(1-x) + bx]$$

and $w$ is a number ranging from 0 to 4.

The preferred metal silicate is where $x$ in the above formula equals 0. The resulting material is a nickel chrysotile, and naturally occurring nickel chrysotile is known as garnierite.

Thus either naturally occurring nickel chrysotile can be employed to promote the subject reaction, or, more preferably, a synthetically prepared nickel chrysotile can be employed. One suitable method of preparing the catalysts of this invention is, as noted above, by the technique of Robson in U.S. Pat. No. 3,729,429. As noted by Robson at the top of Column 4, $Ni_3(OH)_4Si_2O_5$ (garnierite) is found in nature in the form of tubes. Robson acknowledges that synthetic garnierite has been prepared by prior art workers. The nickel chrysotile used in the working examples later in this specification, however, was prepared in accordance with the techniques of Robson and thus the Robson technique is the preferred, although not the only, method of preparing the catalyst for use in the subject invention. In general, this process is to initially synthesize a gel by coprecipitation of the metal oxide or hydroxide with hydrous silica gel in an alkaline medium wherein the pH is above 10, preferably about 12 to 14. The composition of the metal hydroxide layer of the crystal is fixed by selecting the concentration of nickel and ruthenium salts to vary the ratio of nickel to ruthenium as desired. Any water soluble nickel or ruthenium salts can be employed. After the desired gel is produced, it is heated at from about 200° to 350°C., preferably 250° to 275°C., so that the chrysotile product is crystallized from the synthesis gel with rejection of excess water and soluble salts which are removed by filtration and washing. The complex metal silicates as defined above are generally prepared synthetically in hydrated form and are then converted to a dehydrated form by heating prior to use or in situ operation. Since the dehydration reaction is reversible and since water is produced during the methanation reaction, the exact degree of hydration of the catalyst as the reaction proceeds is not known. Thus $w$ in the above formula is defined as ranging from 0 to 4 to indicate that the degree of hydration of the catalyst may vary.

The nickel, ruthenium or mixed nickel-ruthenium chrysotiles are dried to remove surface moisture and may or may not be dehydrated in whole or in part by calcination prior to use. The catalyst also, preferably, undergoes a mild prereduction before use. Calcination is not essential, nor is prereduction with a gas such as hydrogen essential, although varying degrees of calcination and/or prereduction may occur. Since the methanation reaction is operated at elevated temperatures and in the presence of reducing gases, dehydration and reduction of the catalyst will occur during the methanation reaction. Precalcination can suitably occur at temperatures of 300° to 500°C. for 2 to 10 hours. Prereduction using a gas such as $H_2$ at flow rates of 50 to 500 cc/min can also suitably occur at temperatures of 300° to 500°C. for 2 to 10 hours.

The charge stock for the methanation reaction comprises hydrogen and at least one carbon oxide selected from the group consisting of CO and $CO_2$ wherein the molar ratio of hydrogen to combined carbon oxides is at least 2:1. Preferably the hydrogen to combined carbon oxides molar ratio is from about 3:1 to 4:1, although ratios to 10:1 to 100:1 to 1000:1 or more can be employed.

Ideally the methanation reaction proceeds in accordance with Equation I below when CO is the reactive carbon oxide employed.

EQUATION I $$CO + 3H_2 \rightleftharpoons CH_4 + H_2O$$

Referring to Equation I, stoichiometry indicates that the minimum hydrogen to CO mole ratio is 3:1. Hydrogen to CO ratios as low as 2:1 can be used, as noted above, but reduced reaction efficiency results. Higher hydrogen to CO ratios, e.g., above 3:1, tend to discourage side reactions such as the decomposition of CO to form carbon (coke).

If the hydrogen to CO mole ratio is below about 3:1, a secondary water-gas shift reaction can occur as shown by Equation II below:

EQUATION II $$CO + H_2O \rightleftharpoons CO_2 + H_2$$

Methane and $CO_2$ may also be produced as shown in Equation III below.

EQUATION III $$2CO + 2H_2 \rightleftharpoons CH_4 + CO_2$$

If $CO_2$ is present either initially or via Equations II and III above, methane can also be produced as shown in Equation IV below:

EQUATION IV $$CO_2 + 4H_2 \rightleftharpoons CH_4 + 2H_2O$$

Since hydrogen is the more expensive component of the charge stock, it is naturally preferred to keep the $CO_2$ content of the charge stock as low as possible, albeit a charge consisting essentially of $CO_2$ can be employed if desired. The higher molar ratios of $H_2$ to carbon oxides, as noted above, can be used despite the relative high cost of hydrogen, if the methanation reaction (Equations I, III and IV above) is intended as a method of purifying a stream of small concentrations of CO or $CO_2$, e.g., the purification of hydrogen streams destined for ammonia synthesis.

The charge stock for the methanation process of this invention can, of course, be obtained from any suitable source well known to those in the art. For example, if pipeline gas (SNG) is the desired final product, the charge stock for the methanation reaction can be derived from the gasification of coal with steam and oxygen. Initial coal gasification product streams are too low in hydrogen and contain undesirable impurities, especially sulfur compounds which tend to deactivate the catalysts of this invention. A typical coal gasification product on a water-free basis contains about 29% $CO_2$; 19% CO; 38% $H_2$; 13% methane and small amounts of $H_2S$ and nitrogen. Normally these gases are purified to remove sulfur (to less than 1 ppm) and the gases are then subjected to a water-gas shift reaction (Equation II above) to increase the $H_2$ and thus give a product gas stream which is suitable as a charge stock to a methanation reactor, e.g., where the $H_2$ to combined carbon oxides is at least 2:1, preferably 3:1 to 4:1.

Diluent gases such as nitrogen or steam can also be present in the charge stock and the amount of inert material in the charge must be balanced by its usefulness as a heat sink versus the reduced space-time yields of products which are achieved because of the presence of the diluent. In one preferred embodiment of the invention, recycle product consisting primarily of methane is used as the diluent heat sink.

The methanation reaction occurs by contacting the charge stock with the desired catalyst under methanation conditions well known in the art. The methanation reaction is highly exothermic and, as noted above, it is preferred to recycle a portion of the product to serve as a heat sink. This can fortunately be done despite the reversibility of Equations I and III above because thermodynamics greatly favor the production of methane.

The charge stock is usually preheated to a temperature of 400° to 500°F. (204° to 260°C.). This preheated gas is then contacted with the metal chrysotile catalyst of this invention under methanation conditions. By "under methanation conditions" is meant under conditions of temperature, pressure and space velocity for the charge stock whereby the desired methane product is produced by the reaction of $H_2$ and CO and/or $CO_2$. Such methanation conditions are not critical and are well known to those in this art. Typically the temperature of the reaction can be from 400°F. (204°C.), preferably at least 500°F. (260°C.) and can be as high as 900° to 1500°F. (482° to 816°C.). The gaseous hourly space velocity (GHSV) can suitably be from 1 to 100,000 volumes of gas (total gas including recycle product) per volume of reactor per hour, preferably 100 to 10,000 v/v/hr, and most preferably 500 to 5,000 v/v/hr. The reaction pressure is normally atmospheric to 1000 psi; however, increased pressures of up to 10,000 psi or more can be employed. The effect of pressure on reaction kinetics is limited, but increased pressures do allow for the use of smaller reactors, and the economics of increased pressure versus reactor size must be balanced. An upflow fixed bed operation using extrudates, pellets or other suitably shaped and sized catalyst particles can be employed, but obviously, downflow operation or other types of catalyst beds, e.g., fluid beds, can also be employed.

The product from the reactor differs in composition from the charge stock by an increase in the concentration of methane and water and a decrease in the content of hydrogen and carbon oxides. A portion of the product is suitably recycled for admixture with the preheated charge stock to serve as a heat sink in the reactor. The recycle to feed gas volume ratio is usually about 3:1 but can be from 5:1 to 10:1 or more as desired. Steam can, of course, be used to supplant part or all of the recycle gas.

The invention will be further described with reference to the following experimental work.

EXPERIMENTAL WORK

EXAMPLE 1

(Preparation of synthetic nickel chrysotile)

A synthetic nickel chrysotile was prepared by adding 35 grams of Ludox S.A. (DuPont brand name) colloidal silica with stirring to a solution consisting of 60.1 grams of $NiCl_3.6H_2O$ dissolved in 105 cc's of water. pH electrodes were then immersed into the solution and an initial pH recording was made. A solution of 30 grams of NaOH in 70 cc's of water was then added to the $NiCl_3.6H_2O$ - colloidal silica mixture with stirring, until a final pH of 12 was obtained. The final mixture was stirred for an additional 10 minutes and placed into an autoclave where it was heated under autogenic pressure for 24 hours at 500°F. (260°C.). After cooling, the resulting product, a slurry, was removed from the autoclave, filtered and washed with distilled water until free of NaCl. The precipitate was dried at 250°F. (121°C.) overnight. An X-ray diffraction pattern of the product corresponded to the crystalline compound of the formula $Ni_3OH_4Si_2O_5$ (nickel chrysotile). The amount of nickel in the nickel chrysotile on a weight percent basis was 46.31. The X-ray diffraction pattern is shown on Table I below.

TABLE I

| X-RAY POWDER DIFFRACTION PATTERN | |
|---|---|
| d (A.) | I |
| 7.50 | s. |
| 4.50 | m. |
| 3.67 | s. |
| 2.58 | m. |
| 2.46 | m. |
| 2.10 | w. |
| 1.725 | w. |
| 1.545 | m. |
| 1.320 | w. |
| 1.300 | w. |

The sample was submitted for a surface area measurement by the BET method, and the material was found to have a surface area of about 150 m²/g.

It is to be noted that the preparation of nickel chrysotile followed the procedure of Examples 1–11 in the Robson '429 patent except $NiCl_2$ was used in lieu of $MgCl_2$.

EXAMPLE 2

(Supported nickel catalyst)

In this example, a supported nickel catalyst is prepared by dissolving 56.9 grams of $Ni(NO_3)_2.6H_2O$ in 40 cc's of distilled water. The nickel nitrate solution was impregnated onto 25 grams of a 20–40 mesh Davison grade silica (pure $SiO_2$). The catalyst was dried at 250°F. (121°C.) overnight, and then dried at 350°F. (177°C.) for an additional 6 hours. The final concentration of nickel in the silica support was 46.0 weight percent. The catalyst was submitted for a surface area measurement and it was found that the catalyst surface area was in excess of 200 m²/g.

The catalysts of Examples 1 and 2 above were tested for their efficiency in promoting the conversion of CO and hydrogen to methane. In both instances the catalysts were loaded, separately, of course, into a quartz reactor, and a gas consisting of pure CO and hydrogen wherein the molar ratio of hydrogen to CO was equal to 4 was passed through the catalyst bed at a space velocity of 3000 GHSV for a reaction time of four hours. The gas was preheated either to 400° or 500°F. (204° to 260°C.) and the temperature of the catalyst bed and the composition of the outlet gases were measured. Prior to the reaction, each catalyst was reduced in pure hydrogen, flowing at 100 cc's/min rate at 850°F. (454°C.) for a period of about 4 hours. The results are shown in Table II below.

TABLE II

| Catalyst Bed Temperature | | Example 3 Cat: Ni Chrysotile of Example 1 | | | Example 4 Cat: Ni on $SiO_2$ of Example 2 | | |
|---|---|---|---|---|---|---|---|
| °F. | (°C.) | CO | $CH_4$ | $CO_2$ | CO | $CH_4$ | $CO_2$ |
| 400ª | (204) | 80.8 | 19.1 | trace | 81.2 | 18.6 | 0.1 |
| 500ᵇ | (260) | 1.7 | 98.0 | 0.2 | 1.7 | 98.0 | 0.2 |
| 600ᶜ | (316) | 0 | 100 | 0 | 0.8 | 98.8 | 0.3 |
| 700ᶜ | (371) | 0 | 100 | 0 | 0.1 | 99.7 | 0.1 |
| 800ᶜ | (427) | 0 | 100 | 0 | 0 | 100 | 0 |
| 900ᶜ | (482) | 0.2 | 99.4 | 0.3 | 0.5 | 98.6 | 0.8 |
| 1000ᶜ | (538) | 2.7 | 96.4 | 0.8 | 4.3 | 94.2 | 1.4 |

ª Gas was preheated to 400°F. - Initial catalyst temperature was about 400°F.
ᵇ Gas was preheated to 500°F. - Initial catalyst temperature was about 500°F.
ᶜ Catalyst temperature was raised by electric furnace.

Referring to Table II, it can be seen that the nickel chrysotile catalyst of Example 1 was more selective for the conversion of CO to produce methane over a wider temperature range. In addition the catalysts of Examples 3 and 4 were analyzed after the reaction, and no coke was found on the catalyst of Example 3, whereas a small amount of coke was found on the catalyst from Example 4.

An accelerated aging test was next conducted. Fresh batches of each of the catalysts from Examples 1 and 2 above, after reduction as noted for Examples 3 and 4, were next exposed to contact with the hydrogen-CO synthesis gas of Examples 3 and 4 at a GHSV of 3000 at 1500°F. (816°C.) for 2 hours. Examples 3 and 4 were then repeated using these "aged" catalysts, and the results are shown in Table III below. It should be noted in the Examples for Tables II and III the nickel chrysotile was used in the form of 20–40 mesh particles, and the gas composition as shown in Table II above and Table III below normalized assuming the removal of hydrogen.

TABLE III

| Catalyst Bed Temperature | | Example 5 Cat: Ni Chrysotile of Example 1 | | | Example 6 Cat: Ni on SiO$_2$ of Example 2 | | |
|---|---|---|---|---|---|---|---|
| °F. | °C. | CO | CH$_4$ | CO$_2$ | CO | CH$_4$ | CO$_2$ |
| 500 | (260) | 1.5 | 98.2 | 0.3 | 75.0 | 24.6 | 0.3 |
| 600 | (316) | 0 | 100 | 0 | 61.5 | 38.2 | 0.3 |
| 700 | (371) | 0 | 100 | 0 | 43.8 | 56.1 | 0.1 |
| 800 | (427) | 0 | 100 | 0 | 21.4 | 78.2 | 0.4 |
| 900 | (482) | 0.3 | 99.5 | 0.2 | 11.5 | 84.5 | 4.0 |

Referring to Table III above, it can be seen that the accelerated aging had little, if any, effect on the nickel chrysotile catalyst of this invention, whereas the nickel on silica gel catalyst showed substantial aging by the fact that conversion of CO was severely reduced. Examination of the nickel chrysotile catalyst showed that there was no coke present. There was some small coke formation on the nickel on silica gel catalyst of Example 6. The high temperature pretreatment probably collapsed the silica gel structure of the catalyst used for Example 6 showing that the catalyst of this invention has high thermal stability.

The stability of the catalysts of Examples 1 and 2 to high temperatures in the presence of steam was also investigated. Each of the catalysts from Examples 1 and 2 was again reduced in pure hydrogen, flowing at a 100 cc/min rate at 850°F. (454°C.) for a period of 4 hours, after which each catalyst was exposed to a gas stream consisting of 8 percent water in helium at a flow rate of 100 cc/min at 1500°F. (816°C.) for 2 hours. Each of these catalysts was then treated in a manner similar to that shown for Examples 3–6 above, and the results are shown in Table IV below.

TABLE IV

| Catalyst Bed Temperature | | Example 7 Cat: Ni Chrysotile of Example 1 | | | Example 8 Cat: Ni on SiO$_2$ of Example 2 | | |
|---|---|---|---|---|---|---|---|
| °F. | °C. | CO | CH$_4$ | CO$_2$ | CO | CH$_4$ | CO$_2$ |
| 500 | (260) | 1.8 | 97.9 | 0.2 | 78.3 | 20.6 | 1.1 |
| 600 | (316) | 0 | 100 | 0 | 65.0 | 33.7 | 1.2 |
| 700 | (371) | 0 | 100 | 0 | 51.2 | 47.7 | 1.1 |
| 800 | (427) | 0 | 100 | 0 | 32.2 | 66.3 | 1.5 |
| 900 | (482) | 0.3 | 99.3 | 0.4 | 15.1 | 80.4 | 4.4 |
| 1000 | (538) | 2.5 | 96.3 | 1.2 | 17.2 | 74.8 | 8.0 |
| 1100 | (593) | 3.1 | 87.8 | 9.1 | 21.3 | 67.5 | 11.2 |

Referring to Table IV above, it can again be seen that the catalyst of Example 1 held up very well to a high temperature steam pretreatment, whereas the nickel on silica gel catalyst apparently was not able to withstand the temperatures and/or water treatment. The catalysts of Examples 7 and 8 were analyzed for coke formation, and again no coke was found on the catalyst for Example 7, whereas a small amount of coke was found on the catalyst used for Example 8.

EXAMPLE 9

Another batch of catalyst was prepared in accordance with the method of Example 1 above, and the catalyst was extruded in the form of ⅛ inch extrudates. These extrudates were loaded into a 4-foot stainless steel reactor, and a gas obtained by gasification of coal was passed through the catalyst bed at 3000 GHSV. The gas composition is shown on Table V below.

TABLE V

| Gas Composition | Mole % |
|---|---|
| H$_2$ | 66.0 |
| CO | 15.7 |
| CH$_4$ | 12.1 |
| CO$_2$ | 6.2 |
| Sulfur | about 0.1 ppm |

The feed gas was preheated to 550°F. (288°C.) and the catalyst bed temperature during the reaction was about 820°F. (438°C.). The reaction pressure was 300 psig (20 atmospheres). The catalyst was reduced with dry hydrogen at 860°F. (460°C.) for several hours. The composition of the product gas was analyzed after 10 hours of operation and 1260 hours of operation. The results are shown on Table VI below.

TABLE V

| PRODUCT GAS COMPOSITION | | |
|---|---|---|
| Component | Mole Percent After | |
| | 10 hours | 1260 hours |
| H$_2$ | 0.3 | 0.2 |
| CO | 0 | 0 |
| CH$_4$ | 96.3 | 97.2 |
| CO$_2$ | 3.4 | 2.6 |

Referring to Table VI, it can be seen that the catalyst was still active after 1260 hours. It has also been noted that the activity of the catalyst of this invention can be measured by a hot spot which moves through the catalyst bed. However, the hot spot migrates through the bed at ever decreasing rates with time. Based on the data from Example 9 above, it has been mathematically calculated that the predicted life of the catalyst from Example 9 above would be about 1 year using a reactor of approximately 5 feet in length.

In addition to the use of the nickel and/or ruthenium or mixed nickel-ruthenium catalyst described above, per se, the chrysotile can be dispersed in matrices such as silica, alumina or combinations thereof, but obviously the higher temperature stable matrices are preferred. In addition active metals such as nickel and ruthenium can be deposited on the nickel chrysotile catalyst if desired. Obviously excess silica could be added during the preparation so that nickel chrysotile is intimately admixed with the silica during preparation. From the data shown in the Examples above, it is apparent that the disproportionation of CO to CO$_2$ and carbon is avoided using the nickel chrysotile at temperatures up to at least 1500°F. (816°C.). Furthermore, the nickel chrysotile catalyst appears superior to nickel on silica gel in the sense that it maintains 100 percent removal of CO over longer periods of time for a given nickel level at a given temperature and maintains this high activity even when exposed to high temperatures in the presence of reducing gases such as hydrogen and/or CO or in the presence of steam. While it is not certain, it is believed that the superior results of the catalysts of this invention are achieved by the fact that the metals, e.g. nickel, are dispersed through the silica composition through chemistry (their method of preparation) rather than by deposition or dispersion by physical means. Such atomic dispersion results not only in increased life for the catalyst but also in increased selectivity for the conversion of CO to methane.

Resort may be had to such variations and modifications as fall within the spirit of the invention and the scope of the appended claims.

We claim:

1. A process for the production of methane which comprises
contacting a charge stock comprising hydrogen and at least one carbon oxide selected from the group consisting of CO and $CO_2$ wherein the molar ratio of hydrogen to combined carbon oxides is at least 2:1 under methanation conditions with a catalyst comprising a metal silicate characterized as having repeating units having the structural formula:

$$[(1-x)Ni^a + xRu^b]_n (OH)_4Si_2O_5 \cdot wH_2O$$

where $x$ is a number from 0 to 1, this number expressing the atomic fraction of the metals nickel and ruthenium, $a$ is the valence of nickel, $b$ is the valence of ruthenium, $n$ is a number equal in value to that defined by the ratio $$6/[a(1-x) + bx]$$

and $w$ is a number ranging from 0 to 4.

2. A process according to claim 1 wherein the catalyst is nickel chrysotile.

3. A process according to claim 2 wherein the nickel chrysotile is a synthetically prepared nickel chrysotile and has an X-ray powder diffraction pattern substantially the same as follows:

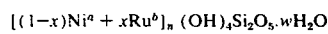

| d (A.) | I |
|---|---|
| 7.50 | s. |
| 4.50 | m. |
| 3.67 | s. |
| 2.58 | m. |
| 2.46 | m. |
| 2.10 | w. |
| 1.725 | w. |
| 1.545 | m. |
| 1.320 | w. |
| 1.300 | w. |

4. A process according to claim 3 wherein the molar ratio of hydrogen to combined carbon oxides in the charge stock is 2:1 to 4:1.

5. A process according to claim 4 wherein the molar ratio of hydrogen to combined carbon oxides in the charge stock is about 3:1 and the methanation conditions include a reaction temperature of from 400° to 1500°F. and a space velocity of from 100 to 10,000 volumes of gas per volume of reactor per hour.

6. A process according to claim 4 wherein the catalyst is in the physical form of tubes.

7. A process according to claim 6 wherein the charge stock consists essentially of $H_2$ and CO and wherein the molar ratio of $H_2$ to CO is at least about 3:1.

8. A process according to claim 7 wherein the charge stock is derived from the gasification of coal.

9. A process according to claim 8 wherein the molar ratio of $H_2$ to combined carbon oxides is from about 2:1 to 4:1.

* * * * *